(12) United States Patent
Sletten et al.

(10) Patent No.: US 11,559,426 B2
(45) Date of Patent: Jan. 24, 2023

(54) SYSTEM INCLUDING A SKIN-ENGAGEABLE ELEMENT OF A MEDICAL APPLIANCE

(71) Applicant: Coloplast A/S, Humlebaek (DK)

(72) Inventors: Carsten Sletten, Espergaerde (DK);
Jais Ask Hansen, Jaegerspris (DK);
Lars Erup Larsen, Maaloev (DK)

(73) Assignee: Coloplast A/S, Humlebaek (DK)

( * ) Notice: Subject to any disclaimer, the term of this patent is extended or adjusted under 35 U.S.C. 154(b) by 277 days.

(21) Appl. No.: 16/955,061

(22) PCT Filed: Dec. 20, 2018

(86) PCT No.: PCT/DK2018/050404
§ 371 (c)(1),
(2) Date: Jun. 18, 2020

(87) PCT Pub. No.: WO2019/120448
PCT Pub. Date: Jun. 27, 2019

(65) Prior Publication Data
US 2020/0383819 A1 Dec. 10, 2020

(30) Foreign Application Priority Data
Dec. 22, 2017 (DK) .......................... PA 2017 71007

(51) Int. Cl.
*A61F 5/443* (2006.01)
*A61F 5/445* (2006.01)

(52) U.S. Cl.
CPC .............. *A61F 5/443* (2013.01); *A61F 5/445* (2013.01)

(58) Field of Classification Search
CPC .......... A61F 5/443; A61F 5/445; A61F 5/448; A61F 13/0253; A61F 4/445; A61M 2202/068; A61M 2202/088
See application file for complete search history.

(56) References Cited

U.S. PATENT DOCUMENTS

| 3,214,502 | A | | 10/1965 | Schaar |
| 3,941,133 | A | | 3/1976 | Chen |
| 4,231,369 | A | * | 11/1980 | Sorensen .............. A61L 24/043 604/336 |

(Continued)

FOREIGN PATENT DOCUMENTS

| CN | 1516568 A | 7/2004 |
| CN | 1720888 A | 1/2006 |

(Continued)

*Primary Examiner* — Guy K Townsend
(74) *Attorney, Agent, or Firm* — Coloplast Corp., Coloplast A/S; Nick Baumann (57) ABSTRACT

A system for preserving functionality of a skin-engageable element for attachment to a skin portion of a user during storage including a skin-engageable element and a protective element having discrete portions projecting therefrom. The discrete portions are adapted to engage with through-going passages in an adhesive layer of the skin-engageable element, and ensure that the passages are open and passable when the protective element is removed before use of the skin-engageable element. A protective element attachable to a proximal adhesive side of a skin-engageable element for attachment to a skin portion of a user is also disclosed.

20 Claims, 7 Drawing Sheets

(56) References Cited

U.S. PATENT DOCUMENTS

| | | | | |
|---|---|---|---|---|
| 4,834,731 | A | * | 5/1989 | Nowak .................. A61F 5/448 604/339 |
| 4,973,323 | A | * | 11/1990 | Kaczmarek ............ A61F 5/448 604/277 |
| 5,013,307 | A | * | 5/1991 | Broida .................. A61F 13/45 604/338 |
| 5,074,851 | A | | 12/1991 | Plass et al. |
| 5,486,158 | A | | 1/1996 | Samuelsen |
| 5,704,905 | A | | 1/1998 | Jensen et al. |
| 5,834,009 | A | | 11/1998 | Sawers et al. |
| 6,206,864 | B1 | | 3/2001 | Kavanagh et al. |
| 6,482,491 | B1 | | 11/2002 | Samuelsen et al. |
| 6,520,943 | B1 | * | 2/2003 | Wagner .................. A61F 5/445 604/338 |
| 7,214,217 | B2 | * | 5/2007 | Pedersen ................ A61F 5/441 604/338 |
| 7,347,844 | B2 | * | 3/2008 | Cline .................... A61F 5/448 604/338 |
| 7,857,796 | B2 | * | 12/2010 | Cline .................... A61F 5/448 604/277 |
| 7,943,812 | B2 | | 5/2011 | Stroebeck et al. |
| 8,277,427 | B2 | | 10/2012 | Edvardsen et al. |
| 8,319,003 | B2 | | 11/2012 | Olsen et al. |
| 8,398,603 | B2 | * | 3/2013 | Thirstrup .............. A61F 5/4404 602/41 |
| 8,399,732 | B2 | | 3/2013 | Oelund et al. |
| 8,449,513 | B2 | * | 5/2013 | Abrams ................ A61F 5/445 604/342 |
| 9,216,104 | B2 | * | 12/2015 | Thirstrup .............. A61F 13/02 |
| 9,770,359 | B2 | * | 9/2017 | Edvardsen ............ A61F 5/445 |
| 10,016,298 | B2 | * | 7/2018 | Thirstrup ............ A61F 13/00051 |
| 10,500,084 | B2 | * | 12/2019 | Hansen ................ A61B 5/6843 |
| 10,531,977 | B2 | * | 1/2020 | Schoess ................ A61F 5/445 |
| 10,786,652 | B2 | * | 9/2020 | Doshi .................. A61F 13/0226 |
| 10,799,385 | B2 | * | 10/2020 | Hansen ................ A61F 5/44 |
| 10,849,781 | B2 | * | 12/2020 | Hansen ................ A61F 5/445 |
| 10,987,243 | B2 | * | 4/2021 | Thirstrup .............. A61F 5/443 |
| 11,096,818 | B2 | * | 8/2021 | Thirstrup .............. A61F 5/445 |
| 2004/0006320 | A1 | * | 1/2004 | Buglino ................ A61F 5/448 604/344 |
| 2004/0106908 | A1 | * | 6/2004 | Leise, Jr. .............. A61F 5/448 604/355 |
| 2004/0171999 | A1 | | 9/2004 | Andersen et al. |
| 2004/0193122 | A1 | * | 9/2004 | Cline .................... A61F 5/448 604/332 |
| 2004/0193123 | A1 | * | 9/2004 | Fenton .................. A61F 5/448 604/344 |
| 2004/0216833 | A1 | * | 11/2004 | Fleming ................ C09J 7/403 156/230 |
| 2005/0054997 | A1 | | 3/2005 | Buglino et al. |
| 2006/0015081 | A1 | | 1/2006 | Suzuki et al. |
| 2007/0035405 | A1 | | 2/2007 | Wada et al. |
| 2008/0038536 | A1 | * | 2/2008 | Strobech ................ C09J 7/20 427/208.4 |
| 2008/0058740 | A1 | * | 3/2008 | Sullivan ................ A61F 13/42 604/361 |
| 2008/0119804 | A1 | * | 5/2008 | Cline .................... A61F 5/445 604/338 |
| 2008/0275327 | A1 | * | 11/2008 | Faarbaek ............ A61B 5/68335 600/382 |
| 2008/0306459 | A1 | | 12/2008 | Albrectsen |
| 2010/0030167 | A1 | * | 2/2010 | Thirstrup .............. A61F 13/02 340/657 |
| 2010/0168693 | A1 | * | 7/2010 | Edvardsen ............ A61F 5/451 604/355 |
| 2010/0324511 | A1 | * | 12/2010 | Dove ..................... A61F 5/445 604/338 |
| 2011/0125115 | A1 | * | 5/2011 | Anders ................ A61L 28/0015 604/344 |
| 2012/0232506 | A1 | * | 9/2012 | Todd .................... A61F 5/445 604/339 |
| 2013/0060184 | A1 | * | 3/2013 | Rea ...................... A61F 13/0246 602/54 |
| 2013/0226116 | A1 | * | 8/2013 | Edvardsen ............ A61F 5/443 604/338 |
| 2013/0231620 | A1 | * | 9/2013 | Thirstrup .......... A61F 13/00051 604/344 |
| 2014/0316360 | A1 | * | 10/2014 | Ekfeldt ................ A61F 5/445 604/338 |
| 2014/0323909 | A1 | | 10/2014 | Kim |
| 2015/0250639 | A1 | * | 9/2015 | Thirstrup ............ A61F 13/42 156/278 |
| 2015/0257923 | A1 | * | 9/2015 | Thirstrup ............ A61F 13/42 604/318 |
| 2015/0359656 | A1 | * | 12/2015 | Hansen ................ A61F 5/443 604/344 |
| 2016/0158056 | A1 | * | 6/2016 | Davis .................. A61F 5/443 29/872 |
| 2016/0256665 | A1 | * | 9/2016 | Doshi ................ A61F 13/00063 |
| 2017/0140103 | A1 | * | 5/2017 | Angelides ............ A61F 5/4404 |
| 2017/0340474 | A1 | * | 11/2017 | Thirstrup .............. A61F 5/445 |
| 2018/0233235 | A1 | * | 8/2018 | Angelides ............ G16H 40/67 |
| 2018/0235801 | A1 | * | 8/2018 | Oellgaard ............ A61F 5/445 |
| 2018/0296384 | A1 | * | 10/2018 | O'Brien ................ A61F 5/443 |
| 2018/0325718 | A1 | * | 11/2018 | Ekfeldt ................ A61F 5/445 |
| 2019/0142623 | A1 | * | 5/2019 | Schoess ................ A61F 5/4404 604/336 |
| 2019/0192332 | A1 | * | 6/2019 | Hansen ................ A61B 5/7475 |
| 2019/0192333 | A1 | * | 6/2019 | Hansen ................ G01N 27/20 |
| 2019/0192334 | A1 | * | 6/2019 | Hansen ................ A61F 5/4404 |
| 2019/0374213 | A1 | * | 12/2019 | Goldsmith ............ A61F 2/042 |
| 2020/0015996 | A1 | * | 1/2020 | Schertiger ............ A61F 5/4401 |
| 2020/0100931 | A1 | * | 4/2020 | Schoess ................ A61F 5/443 |
| 2020/0188161 | A1 | * | 6/2020 | Seres .................... G01K 13/00 |
| 2020/0246174 | A1 | * | 8/2020 | Hansen ................ A61F 5/4404 |
| 2020/0246175 | A1 | * | 8/2020 | Hansen ................ G01M 3/16 |
| 2020/0246177 | A1 | * | 8/2020 | Hansen ................ A61B 5/4851 |
| 2020/0253777 | A1 | * | 8/2020 | Jones .................. A61F 5/443 |
| 2020/0297524 | A1 | * | 9/2020 | Hunt .................... A61F 5/445 |
| 2020/0337879 | A1 | * | 10/2020 | Donovan ............ A61F 5/443 |
| 2020/0337884 | A1 | * | 10/2020 | Donovan ............ A61F 5/448 |
| 2020/0337885 | A1 | * | 10/2020 | Donovan ............ A61F 5/443 |
| 2020/0375782 | A1 | * | 12/2020 | Hansen ................ A61F 5/4404 |
| 2020/0375783 | A1 | * | 12/2020 | Hansen ................ A61B 5/742 |
| 2020/0383819 | A1 | * | 12/2020 | Sletten ................ A61F 5/443 |
| 2020/0383821 | A1 | * | 12/2020 | Hansen ................ A61F 5/4404 |
| 2021/0000635 | A1 | * | 1/2021 | Hansen ................ A61F 5/44 |
| 2021/0000636 | A1 | * | 1/2021 | Hansen ................ A61F 5/445 |
| 2021/0015653 | A1 | * | 1/2021 | Hansen ................ A61B 5/4851 |
| 2022/0000652 | A1 | * | 1/2022 | Thirstrup ............ A61F 13/02 |
| 2022/0378602 | | * | 12/2022 | Hansen ................ A61F 5/445 |

FOREIGN PATENT DOCUMENTS

| | | | |
|---|---|---|---|
| CN | 101052363 A | 10/2007 | |
| CN | 101217923 A | 7/2008 | |
| CN | 101394817 A | 3/2009 | |
| CN | 104144661 A | 11/2014 | |
| JP | 2001087299 | * 3/2001 | ............ A61F 5/445 |
| JP | 2001087299 A | 4/2001 | |
| WO | 9936017 A1 | 7/1999 | |
| WO | 2007000168 A1 | 1/2007 | |
| WO | 2014086369 A1 | 6/2014 | |
| WO | 17067560 A1 | 4/2017 | |

* cited by examiner

SYSTEM INCLUDING A SKIN-ENGAGEABLE ELEMENT OF A MEDICAL APPLIANCE

BACKGROUND

Stomal output often contains body fluids and visceral contents that are aggressive to both the skin surface of users and to ostomy appliances, in particular such fluids have a detrimental effect on the efficiency and integrity of the adhesive materials that are applied to attach an ostomy appliance to a user's skin surface. In addition, some users may choose or have to wear their device for prolonged periods of time. For users of ostomy appliances safe, reliable, efficient and easy-to-use devices are highly desirable. Numerous attempts from many providers have been made to market ostomy devices that meet such demands, including demands for an increase in wear time before change of the ostomy device is needed, but improved products being sufficiently efficient in achieving a satisfactory wear time of ostomy devices for all ostomy types, continues to be in high demand.

A particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output 'underneath' the adhesive leads to deterioration and/or weakening of the adhesive material carrying the weight and providing the seal of the ostomy appliance. Often such adhesive failure happens surprisingly fast and is only detectable for the user once the failure has already become so severe that leakage occurs, requiring immediate change of the ostomy appliance and possibly also of the user's clothes.

Users and health care professionals alike would welcome improvements in ostomy devices to reduce or eliminate the occurrence of sudden leakage incidents and meet demands for increasingly reliable products.

SUMMARY

The present disclosure provides aspects and embodiments of a system including a skin-engageable element of an ostomy appliance according to the appended claims.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which embodiments are illustrated according to which the invention may be practiced. In this regard, directional terminology, such as "top," "bottom," "front," "back," "leading," "trailing," etc., is used with reference to the orientation of the Figure(s) being described. Because components of embodiments can be positioned in different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A person having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device or component, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being a portion adjacent to the centre of the component. In analogy, "outermost" should be interpreted as a portion of a component forming an outer edge or outer contour of a component and/or a portion being adjacent to that outer edge or outer contour.

The use of the phrase "substantially" as a qualifier to certain features or effects in this disclosure is intended to simply mean that any deviations are within tolerances, such as manufacturing tolerances, that would normally be expected by the skilled person in the relevant field.

In this disclosure, the wordings "first layer of adhesive material" and "first adhesive layer" may be used interchangeably without any differentiated meaning or interpretation being intended, unless specifically stated to deviate from this. The same applies in relation to the wordings "second layer of adhesive material" and "second adhesive layer".

In this disclosure, the wording "discrete" is intended to mean a thing that constitutes a separate entity or part. Alternatively, or additionally, it means a thing that is consisting of distinct or unconnected elements. Thus, by defining e.g. through-going passages as "discrete", it is clear these do not form interconnected elements, e.g. do not form interconnected cavities or passages.

In one aspect, the present disclosure relates to a system for preserving functionality of a skin-engageable element of an ostomy appliance during storage according to claim 1.

A skin-engageable element includes a carrier sheet and comprises a first major proximal side and a second major distal side. The skin engageable element includes, on the first major proximal side, a first layer of adhesive material, which is configured for adhesion of the skin-engageable element to a peristomal skin portion of a user. The first layer of adhesive material includes two or more discrete through-going passages.

A protective element, which is removably attached to the first major proximal side of the skin-engageable element, includes a sheet material comprising two or more discrete portions projecting substantially axially from a major surface of the sheet material. Each of the two or more discrete projecting portions of the sheet material is adapted to engage with one of the through-going passages in the first layer of adhesive material. Each of the through-going passages in the first layer of adhesive material is thereby open and passable, when the removable protective element is removed from the skin-engageable element before attachment thereof to a user's skin surface. The term 'passable' should be understood as 'allowing for passage through'. In one example, the (open) through-going passage is passable for moisture and/or liquid substances, such as (but not limited to) drops of liquid water, sweat transpiring from the user's skin, mucous from a user's stoma and body wastes, such as stomal output from a stoma. Also, the through-going passages can alternatively or additionally be configured to allow for relatively solid material pieces to pass through (including "solid" components of stomal output, particularly w.r.t. colostomies).

Providing a system according to the disclosure including a protective element including discrete portions projecting substantially axially from a major surface of the sheet material, entails several advantageous effects. One effect includes that it is ensured that the functionality of the skin-engageable element of the ostomy appliance is preserved throughout a storage period of the element. A "storage period" should be understood in the sense that the components of an ostomy appliance, including a skin-engageable element (such as a base plate), should normally have a shelf-life for up to five years or 60 months, typically at least three years or 36 months.

The two or more discrete portions projecting substantially axially from a major surface of the sheet material are configured to engage with the through-going passages in the first layer of adhesive material. The two or more discrete projecting portions of the protective element are configured to face the first major proximal side of the skin-engageable element, and to be in direct contact with the adhesive material of the skin-engageable element during storage. In other words, the projecting portions of the protective element of the disclosed system do not entail or create a space between a proximal (adhesive) surface of the skin-engageable element and a distal surface of the protective element including the projections.

Adhesive materials typically applicable for a skin-engageable element of an ostomy appliance according to the present disclosure are often relatively soft and pliant. Therefore, the through-going passages in the adhesive material may over time, such as over the shelf-life of the ostomy appliance, become impassable or completely closed (i.e. no longer "allowing for passage through") due at least to the characteristics of the adhesive materials and/or the storage and/or handling conditions during the shelf-life of the skin-engageable element. In one example, such adhesive material can be prone to slowly flow or seep, e.g. due to changes in the temperature and/or pressure conditions of the surroundings.

If, as an example, a through-going passage is perceived as forming or comprising an internal "wall surface" in the layer of adhesive material, the adhesive material may begin to "run", e.g. migrate and/or seep, causing the internal "wall surface" of the through-going passage to collapse, and thereby making the through-going passage impassable. This is not per se an instantaneous problem, but can certainly become an issue over the course of the shelf-life of the ostomy appliance including a skin-engageable element according to the disclosure.

Providing a protective element of the system according to the present disclosure ensures that the internal "wall surfaces" in through-going passages of the adhesive material can be supported throughout the period of the shelf-life of the ostomy appliance, such that the through-going passages are "kept" or sustained in their intended shape or configuration, and thus are available when the skin-engageable element of the ostomy appliance is to be used.

In embodiments, the sheet material of the protective element comprises a thermoformable material. In embodiments, the sheet material of the protective element comprises a polyethylene terephthalate material (such as APET) in a thickness ranging between 100-200 μm, such as 125-175 μm, such as 150 μm.

In embodiments, each of the two or more discrete portions projecting substantially axially from a major surface of the sheet material of the protective element is formed with a generally rounded outer contour, such as when considered in a cross-sectional top view. In embodiments, such generally rounded contour reflects an internal diameter of the projecting portion of about 1-3 mm, such as 1.5-2.5 mm, such as 2 mm.

Another advantageous effect of the system of the present disclosure includes to protect the materials or components of the skin-engageable element of the ostomy appliance provided on the first major proximal side, at a position "underneath" a through-going passage in the adhesive material. In one non-limiting example, such material or components can include materials or components which are configured to help create a reaction, such as a signal, when brought into contact with a liquid substance or solid material passing through one or more of the through-going passages in the layer of adhesive material.

A yet further advantageous effect of the system of the present disclosure is that any of the adhesive material at the internal "wall surface" of the through-going passages is protected from contamination by dust or other small particles, which could otherwise gradually reduce the adhesive effect (adhesiveness) of the material.

The first layer of adhesive material can be made of a first composition. The first composition can comprise one or more polyisobutenes and/or styrene-isoprene-styrene. The first composition can comprise one or more hydrocolloids. The first composition can be a pressure sensitive adhesive composition suitable for medical purposes comprising a rubbery elastomeric base and one or more water soluble or water swellable hydrocolloids. The first composition can comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer can for example be a styrene-butadiene-styrene block copolymer or a styrene-isoprene-styrene block copolymer. In embodiments, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. In embodiments, the polybutene is polyisobutylene (PIB). Suitable hydrocolloids for incorporation in the first composition are selected from naturally occurring hydrocolloids, semisynthetic hydrocolloids and synthetic hydrocolloids. The first composition can comprise 20-60% hydrocolloids. A preferred hydrocolloid is carboxymethylcellulose (CMC). The first composition can optionally contain other components, such as fillers, tackifiers, plasticizers, and other additives.

In embodiments, the skin-engageable element of the ostomy appliance includes a second layer of adhesive material distal to the first layer of adhesive material. The second layer of adhesive material may include two or more discrete through-going passages. The two or more discrete through-going passages may be coincident with the two or more discrete through-going passages of the first layer of adhesive material.

In embodiments, the first and the second layers of adhesive material can be configured to at least partly overlap (or be "on top" of one another). In embodiments, the first layer of adhesive material is of a different composition than the second layer of adhesive material. Providing different compositions of the first and the second adhesive layer can help to provide a more versatile skin-engageable element. In addition, in some embodiments, providing different compositions of the first and the second adhesive layers can help to either amplify, or, alternatively, to attenuate, the desired effect(s) of each of the individual first and second layers of adhesive material. In embodiments, the compositions of the first and second layers of adhesive material may include (be composed of/comprise) identical materials, but in different percentages, thereby making the first and second layer compositions different from each other.

In embodiments, the second layer of adhesive material is adapted to be particularly resistant to stomal output to avoid degradation of the second adhesive material. In embodiments, the second layer of adhesive material is adapted to be particularly suitable for being applied at an outlying portion of the skin-engageable element of the ostomy appliance, e.g. an adhesive having a high initial tack such as an acrylate-based type adhesive. In embodiments including both a first layer of adhesive material and a second layer of adhesive material, the first layer of adhesive material can advantageously be adapted to be particularly resistant to stomal output, and the second layer of adhesive material is advantageously adapted to be particularly suitable for ensuring a strong adhesion to the skin surface.

In embodiments, the first layer of adhesive material and the second layer of adhesive material are provided in a layered relationship with each other, such that one of the layers is provided "on top" of the other layer. As such, the layers can be substantially completely overlapping or only partially overlapping, including overlapping only in distinct zones separated from each other. In other embodiments, the first layer of adhesive material and the second layer of adhesive material are provided in a "side-by-side" relationship with each other, such that one of the layers is provided "next to" the other layer, such as (but not limited to) one adhesive material being provided annularly around the other adhesive material.

When two or more discrete through-going passages of the second layer of adhesive material are coincident with the two or more discrete through-going passages of the first layer of adhesive material, the two or more discrete projecting portions of the protective element are configured to engage with the through-going passages in both the first layer of adhesive material, and with the coincident through-going passages in the second layer of adhesive material. Thereby, the effects and benefits described above for a skin-engageable element including one (first) layer of adhesive material can be equally obtained for a skin-engageable element including two (first and second) layers of adhesive material. It will be understood that the term "coincident" should be interpreted such that a through-going passage in the first layer of adhesive material is right "on top" or "beneath" a through-going passage in the second layer of adhesive material without any substantial lateral offset between the passages of the two layers of adhesive material. Furthermore, by being "coincident" any liquid substance or piece of solid material passing through a passage of one of the adhesive layers can continue through a coincident passage of the second layer of adhesive material, without being hindered in such passing movement, or be prone to become stuck in the passage.

The compositions of the first and/or the second adhesive material of the skin-engageable element may influence requirements for how the shape and/or structure, such as, or including, an outer contour, of the two or more discrete projecting portions of the protective element supports the adhesive material. Thus, alternatively or additionally to having a rounded outer contour, in embodiments, the shapes of the two or more discrete projecting portions are optimized to provide support of the adhesive material according to the characteristics of the adhesive material. Such optimization is provided during manufacture of the system of the present disclosure, particularly during manufacture of the protective element.

In embodiments, the discrete projecting portions projecting from the protective element include a plurality of discrete projecting portions. In embodiments, the plurality of discrete portions projecting from the protective element is distributed in a circle pattern. In embodiments, the plurality of discrete portions projecting from the protective element includes 2-50 discrete projecting portions. In embodiments, the plurality of discrete portions the plurality of discrete portions projecting from the protective element includes 21-30 discrete projecting portions.

In embodiments, the skin-engageable element further includes one or more electrodes provided distal to the first layer of adhesive material. The one or more electrodes is/are accessible from the first major proximal side of the skin-engageable element, through each of the two or more discrete through-going passages in the first layer of adhesive material.

In embodiments, the skin-engageable element further includes one or more electrodes provided distal to the first layer of adhesive material and proximal to the second layer of adhesive material. Thus, the one or more electrodes may be provided in a sandwiched structure between the first and second layer of adhesive material, i.e. on the distal side of the first layer of adhesive material and on the proximal side of the second layer of adhesive material. In another embodiment, the one or more electrodes may be provided on the distal side of the second layer of adhesive material. The one or more electrodes is/are accessible from the first major proximal side of the skin-engageable element, through each of the two or more discrete through-going passages in the first layer of adhesive material. In another embodiment, the one or more electrodes are provided on the distal side of the second adhesive layer. Thereby, the one or more electrodes is/are accessibly from the first major proximal side of the skin-engageable element through each of the two or more discrete and coincident through-going passages in the first and second layers of adhesive material. In non-limiting examples, the one or more electrodes can function as one or more sensor(s), e.g. two of the one or more electrodes may function as a sensor.

In embodiments, the one or more electrodes is/are provided in an electrode assembly or electrode layer, wherein the electrode layer includes material of the electrode(s) provided in or on a layer of polyurethane material. In embodiments, the electrode layer includes an ethylene vinyl acetate (EVA) material.

In embodiments, the electrode layer further includes an adhesive material for attachment of the electrode layer to the proximal side of the carrier sheet. In embodiments, the adhesive material is provided as a tie layer on a distal surface of the electrode layer, or on the proximal side of the carrier sheet. Other ways of attaching the electrode layer to the proximal side of the carrier sheet, such as welding, are also acceptable, provided the attachment or the attaching process does not influence the one or more electrodes or any other characteristic of the electrode layer or other parts of the system.

In embodiments, at least a portion of the electrode layer is adapted to be moisture permeable. In one embodiment, the entire electrode layer is adapted to be moisture permeable. In embodiments, only a portion of the electrode layer is adapted to be moisture permeable. The electrode layer can advantageously be made moisture permeable to e.g. provide for an option of embedding the one or more electrodes in the material of the electrode layer. Thus, in embodiments, one or more electrodes are embedded in the electrode layer. In one embodiment, the electrode layer includes a substantially planar distal surface and a substantially planar proximal surface, with the one or more electrodes embedded in the electrode layer.

In embodiments, the one or more electrodes is/are provided in one and the same plane of the electrode layer. This provides a relatively simple structure, which is advantageous to reduce complexity and manufacturing costs.

In embodiments, the one or more electrodes is/are printed on to one of the planar surfaces of the electrode layer. In one embodiment, the one or more electrodes is/are printed on to the planar proximal surface of the electrode layer, such as on a support layer of the electrode layer.

In embodiments, the one or more electrodes include(s) a silver material and/or a carbon black material. In embodiments, the one or more electrodes include(s) one or more inks containing a carbon black material. In one embodiment, carbon black containing electrodes are printed onto the electrode layer. In embodiments, a thickness of each of the one or more electrodes is approximately 20 µm. Alternatively, the one or more electrodes can be applied by a laminating process or by a punching process. Alternatively, or additionally, the one or more electrodes can be provided from solution-based materials, such as organic semiconductors, inorganic semiconductors, metallic conductors, nanoparticles, nanotubes and others.

In embodiments including one or more electrodes, the system according to the present disclosure is further advantageous in that the protective element protects the electrically conductive material of the one or more electrodes from oxidation, because the one or more electrodes are not exposed to oxygen of the ambient air during storage. Thus, the protective element of the system further also helps to preserve the functionality of the one or more electrodes during the shelf-life of the skin-engageable element. In embodiments, a distal-most outer surface portion of each of the two or more discrete projecting portions of the protective element configures to contact and thus further protect the one or more electrodes of the electrode layer.

In embodiments, a total second surface area of the second layer of adhesive material is greater than a total first surface area of the first layer of adhesive material. In embodiments, the second layer of adhesive material has a larger surface area than the first layer of adhesive material. The term "total (first/second) surface area" is intended to mean an entirety of either the proximal surface of the first or second adhesive layer, or an entirety of the distal surface of the first or second adhesive layer (but not both).

In embodiments, a total third surface area of the electrode layer corresponds substantially to the total second surface area of the second layer of adhesive material.

In embodiments, a total third surface area of the electrode layer is smaller than the total second surface area of the second layer of adhesive material.

In embodiments, a total third surface area of the electrode layer corresponds substantially to the total first surface area of the first layer of adhesive material.

In embodiments, a total third surface area of the electrode layer is smaller than the total first surface area of the first layer of adhesive material.

In embodiments, the carrier sheet includes a woven or a non-woven material. In embodiments, the carrier sheet is a thermoplastic polymer film. In embodiments, the carrier sheet includes an elastic material. In embodiments, the carrier sheet is suitably capable of transmitting moisture and may e.g. be made from polymers such as polyolefin types e.g. PE, PP or polybutylene, polyamide such as nylon, polyurethane, polyvinyl acetate, polyvinyl chloride, fluorinated polyvinyl compound, polyvinylidene chloride, polyvinyl alcohol, ethylene vinyl acetate, cellulose acetate or other thermoplastic polysaccharides, polyether block amides such as PEBAX® from Arkema, France, block copolymers like styrene-isoprene-styrene block copolymers or ethylene acrylate block copolymers, polyesters such as polyethylene terephthalate (PET) or derivates thereof and any laminates from such polymers. In other embodiments, the carrier sheet includes a thin foam layer made from e.g. polyurethane, polyethylene or polyvinyl acetate.

In embodiments, the second major distal side of the skin-engageable element of the ostomy appliance further includes a first coupling half provided on the carrier sheet and adapted to be coupled to a second coupling half on a collecting bag for collecting body waste from an ostomy. The first coupling half is configured for releasable coupling with a second coupling half provided on the body waste collecting bag.

In embodiments, the first coupling half is a flange adapted to provide a surface for attaching the second coupling half in the form of an adhesive flange provided on a waste collecting bag. In embodiments, the first coupling half is configured as a flexible, planar annular flange optionally including an adhesive. The first coupling half is adapted to couple with the second coupling half, which is provided around an inlet opening of a waste collecting bag by means of an adhesive. The adhesive coupling can provide a releasable or a permanent adhesive coupling engagement between the skin-engageable element and the waste collecting bag.

In embodiments, the first coupling half is an annular ring including an upstanding flange, protruding perpendicularly from the second major distal side for attachment to a second coupling half in the form of a coupling ring provided on the waste collecting bag. In one embodiment, the annular ring is attached to the second major distal side formed by the carrier sheet. In embodiments, the first coupling half is attached by an adhesive or by welding, but other ways of attaching to the second major distal side, including to the carrier sheet, are acceptable.

In embodiments, the first coupling half includes an annular ring extending substantially perpendicularly from a flange, and wherein an outermost periphery of the flange is substantially at a same radial distance from a center of the skin-engageable element as an outermost periphery of the electrode layer. In embodiments, the annular ring and flange of the first coupling half define and "enclose" a center portion of the first layer of adhesive material.

In embodiments, the system according to the present disclosure includes a collecting bag for collecting body waste, where the collecting bag is configured to be attached to the second major distal side of the skin-engageable element. In embodiments, the waste collecting bag is permanently, i.e. not couplable, attached to the second major distal side of the skin-engageable element.

In embodiments, at least the skin-engageable element of the ostomy appliance includes a central opening for receiving for accommodating a stoma and/or for allowing body waste to pass through and into a collecting bag.

The embodiments of the system according to the present disclosure, including a protective element comprising a sheet material having two or more discrete portions projecting substantially axially from a major surface of the sheet material, are advantageously utilized in an ostomy system and devices thereof, such as an ostomy system including a base plate, a monitor device, and optionally one or more accessory devices.

The above-mentioned ostomy system includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein in relation to the provision of one or more electrodes. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The embodiments of the system of the present disclosure are advantageously used in an ostomy system comprising an ostomy appliance including a base plate and/or a sensor assembly part, a monitor device, and optionally one or more accessory devices which either alone or together facilitate reliable determination of the nature, severity and rapidness of moisture propagation in the adhesive material provided for attaching the base plate and/or the sensor assembly part to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

In embodiments, the ostomy appliance comprises a base plate and an ostomy pouch (also referred to as an ostomy bag, a collecting bag for body waste or a waste collecting bag). The ostomy appliance can be a colostomy appliance, an ileostomy appliance or a urostomy appliance. The ostomy appliance can be a two-part ostomy appliance, i.e. the base plate and the ostomy pouch may be releasably coupled e.g. with a mechanical and/or an adhesive coupling, e.g. to allow that more than one ostomy pouch can be utilized (exchanged) with a single base plate. The ostomy appliance can be a one-piece ostomy appliance, i.e. the base plate and the ostomy pouch are fixedly attached to each other. The base plate is configured for coupling to skin surrounding the stoma, such as a peristomal skin area.

In embodiments, the base plate and/or the sensor assembly part of the ostomy appliance comprises a first adhesive layer, such as the first layer of adhesive material as described above, in embodiments also denoted center adhesive layer. During use, the first adhesive layer adheres to the user's skin (peristomal area) and/or to additional seals, such as sealing paste, sealing tape and/or sealing ring. In embodiments, the first adhesive layer comprises a stomal opening with a center point.

In embodiments, the first adhesive layer comprises a plurality of sensor point openings. For example, the first adhesive layer may include through going passages, as described above, such as two or more discrete through-going passages. The through going passages of the first adhesive layer may form the plurality of sensor point openings. A sensor point opening of the first adhesive layer is optionally configured to overlap a part of an electrode, e.g. to form a sensor point.

In embodiments, the sensor point openings of the first adhesive layer comprise primary sensor point openings. The primary sensor point openings may comprise one or more primary first sensor point openings and one or more primary second sensor point openings, where the primary first sensor point openings are configured to overlap parts of an electrode and the primary second sensor point openings are configured to overlap parts of another electrode different from the electrode at least partly overlapped by the primary first sensor point openings.

In embodiments, the sensor point openings of the first adhesive layer comprise secondary sensor point openings. The secondary sensor point openings can comprise one or more secondary first sensor point openings and one or more secondary second sensor point openings, where the secondary first sensor point openings are configured to overlap parts of an electrode and the secondary second sensor point openings are configured to overlap parts of another electrode different from the electrode at least partly overlapped by the secondary first sensor point openings.

In embodiments, the sensor point openings of the first adhesive layer comprise tertiary sensor point openings. The tertiary sensor point openings can comprise one or more tertiary first sensor point openings and one or more tertiary second sensor point openings, where the tertiary first sensor point openings are configured to overlap parts of an electrode and the tertiary second sensor point openings are configured to overlap parts of another electrode different from the electrode at least partly overlapped by the tertiary first sensor point openings.

In embodiments of the system, the first adhesive layer has a substantially uniform thickness. In embodiments, the first adhesive layer has a thickness in the range from 0.1 mm to 1.5 mm, e.g. in the range from 0.2 mm to 1.2 mm.

The first adhesive layer can have a primary thickness in a primary part of the first adhesive layer, e.g. in a primary region within a primary radial distance or in a primary radial distance range from the center point of the stomal opening. The primary thickness can be in the range from 0.2 mm to 1.5 mm, such as about 1.0 mm. The primary radial distance can be in the range from 20 mm to 50 mm, such as in the range from 25 mm to 35 mm, e.g. 30 mm.

The first adhesive layer can have a secondary thickness in a secondary part of the first adhesive layer, e.g. in a secondary region outside a secondary radial distance or in a secondary radial distance range from the center point of the stomal opening. The secondary thickness can be in the range from 0.2 mm to 1.0 mm, such as about 0.5 mm. The secondary radial distance can be in the range from 20 mm to 50 mm, such as in the range from 25 mm to 35 mm, e.g. 30 mm.

In embodiments, the base plate and/or the sensor assembly part comprises a second layer of adhesive material, such as the second layer of adhesive material as described above, in embodiments also denoted rim adhesive layer. In embodiments, the second layer of adhesive material has a second radial extension that is larger than a first radial extension of the first adhesive layer at least in a first angular range of the base plate and/or the sensor assembly part. Accordingly, a part of a proximal surface of the second layer of adhesive material can be configured for attachment to the skin surface of a user. The part of a proximal surface of the second layer of adhesive material configured for attachment to the skin surface of a user is also denoted "the skin attachment surface" of the second adhesive layer. In embodiments, the second layer of adhesive material comprises a stomal opening with a center point aligned with the stomal opening in the first layer of adhesive material.

The second adhesive layer may be made of a second composition. The second composition may comprise one or more polyisobutenes and/or styrene-isoprene-styrene. The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less moldable than the first adhesive layer. The second adhesive layer may provide a second barrier against leakage.

In embodiments, the second layer of adhesive material has a substantially uniform thickness. In embodiments, the second layer of adhesive material has a thickness in the range from 0.1 mm to 1.5 mm, e.g. in the range from 0.2 mm to 1.0 mm, such as 0.5 mm, 0.6 mm, or 0.7 mm.

In embodiments, the base plate and/or the sensor assembly part may comprise one or more electrodes, such as the one or more electrodes described above, such as a plurality of electrodes, such as two, three, four, five, six, seven or more electrodes. In embodiments, the electrodes, e.g. some or all the electrodes, are arranged between the first adhesive layer and the second adhesive layer. In embodiments, the electrodes are provided distal to the first adhesive layer. In embodiments, the electrodes are provided proximal to the second adhesive layer. In embodiments, the electrodes are arranged in an electrode assembly, e.g. an electrode layer. In embodiments, an electrode comprises a connection part for connecting the electrode to other components and/or interface terminals/terminal elements. In embodiments, an electrode comprises one or more conductor parts and/or one or more sensing parts. A conductor part may be considered part of an electrode connecting two or more sensing parts, and/or connecting a sensing part with a connection part of the respective electrode. A sensing part may be considered a part of the electrode being suitable for sensing, e.g. liquid, such as liquid content, and/or output, such as output resulting from a leakage, or an imminent leakage. The sensing part may be suitable for sensing e.g. by its shape, said shape potentially being circular, oval, or rectangular. Thus, the conductor part may conduct a signal arising from the sensing part. An electrode may comprise alternating conductor parts and sensing parts. In embodiments, the electrode assembly or electrode layer is arranged between the first adhesive layer and the second adhesive layer. In embodiments, the base plate and/or the sensor assembly part, e.g. the electrode assembly comprises a first electrode, a second electrode and optionally a third electrode. In embodiments, the base plate and/or the sensor assembly part, e.g. the electrode assembly comprises a fourth electrode and/or a fifth electrode. In embodiments, the base plate and/or the sensor assembly part, e.g. the electrode assembly optionally comprises a sixth electrode. In embodiments, the base plate and/or the sensor assembly part, e.g. the electrode assembly, comprises a ground electrode. In embodiments, the ground electrode comprises a first electrode part. In embodiments, the first electrode part of the ground electrode forms a ground for the first electrode. In embodiments, the ground electrode comprises a second electrode part. In embodiments, the second electrode part of the ground electrode forms a ground for the second electrode. In embodiments, the ground electrode comprises a third electrode part. In embodiments, the third electrode part of the ground electrode forms a ground for the third electrode. In embodiments, the ground electrode comprises a fourth electrode part. In embodiments, the fourth electrode part of the ground electrode forms a ground for the fourth electrode and/or the fifth electrode.

In embodiments, the first electrode forms an open loop. In embodiments, the second electrode forms an open loop and/or the third electrode forms an open loop. In embodiments, the fourth electrode forms an open loop. In embodiments, the fifth electrode forms an open loop.

In embodiments, the electrode assembly comprises a support layer, also denoted a support film. In embodiments, one or more electrodes are formed, e.g. printed, on the proximal side of the support layer. In embodiments, one or more electrodes are formed, e.g. printed, on the distal side of the support layer. In embodiments, the electrode assembly comprises a stomal opening with a center point.

In embodiments, the base plate and/or the sensor assembly part, such as the electrode assembly may comprise a masking element configured to insulate at least parts (portions) of the electrodes from the first adhesive layer of the base plate and/or the sensor assembly part. In embodiments, the masking element comprises one or more, such as a plurality of, sensor point openings. In embodiments, the sensor point openings comprise primary sensor point openings and/or secondary sensor point openings. In embodiments, the sensor point openings comprise tertiary sensor point opening(s). In embodiments, the sensor point openings comprise quaternary sensor point opening(s). In embodiments, a sensor point opening of the masking element overlaps at least one electrode of the electrode assembly when seen in the axial direction, e.g. to form a sensor point. For example, a primary sensor point opening can overlap a part of the ground electrode and/or a part (portion) of the fourth electrode. In embodiments, a secondary sensor point opening overlaps a part (portion) of the fourth electrode and/or a part of the fifth electrode. In embodiments, a tertiary sensor point opening overlaps a part (portion) of the fifth electrode and/or a part of the ground electrode.

To provide additional support and to secure against leakage of stomal fluids from deep or recessed stomas, convex ostomy products are widely available. The system of the present disclosure is also applicable to such convex ostomy products. Thus, in embodiments, the skin-engageable element of the system further comprises a convex supporting device defining a convex contour of the skin-engageable element, such as a convex contour of the first major proximal side of the skin-engageable element. In embodiments, the convex supporting device is provided distal to the first layer of adhesive material. In embodiments, the first layer of adhesive material is provided, such as by a coating, on at least a portion of a proximal surface of the convex supporting element. In embodiments, the convex supporting device is provided distal to both the first layer of adhesive material and the second layer of adhesive material. In embodiments, the convex supporting device is provided distal to the first layer of adhesive material and/or to the second layer of adhesive material, and proximal to the carrier sheet of the skin-engageable element.

In relation to users suffering from hernia, i.e. the phenomenon that a bodily structure (e.g. the intestine) protrudes through a rupture in smooth muscle tissue surrounding it, experience shows that it is often difficult to attach a 'standard' ostomy appliance to the skin surface where the hernia is located in a manner that provides satisfactory protection against leakage from stomal fluids. Applicant's earlier application, published as WO 2014/086369, discloses a partially concave ostomy appliance targeting ostomists having a hernia. The system of the present disclosure is also applicable to ostomy appliance such as those described in the WO 2014/086369 publication.

DETAILED DESCRIPTION OF THE DRAWINGS

Figure 1:
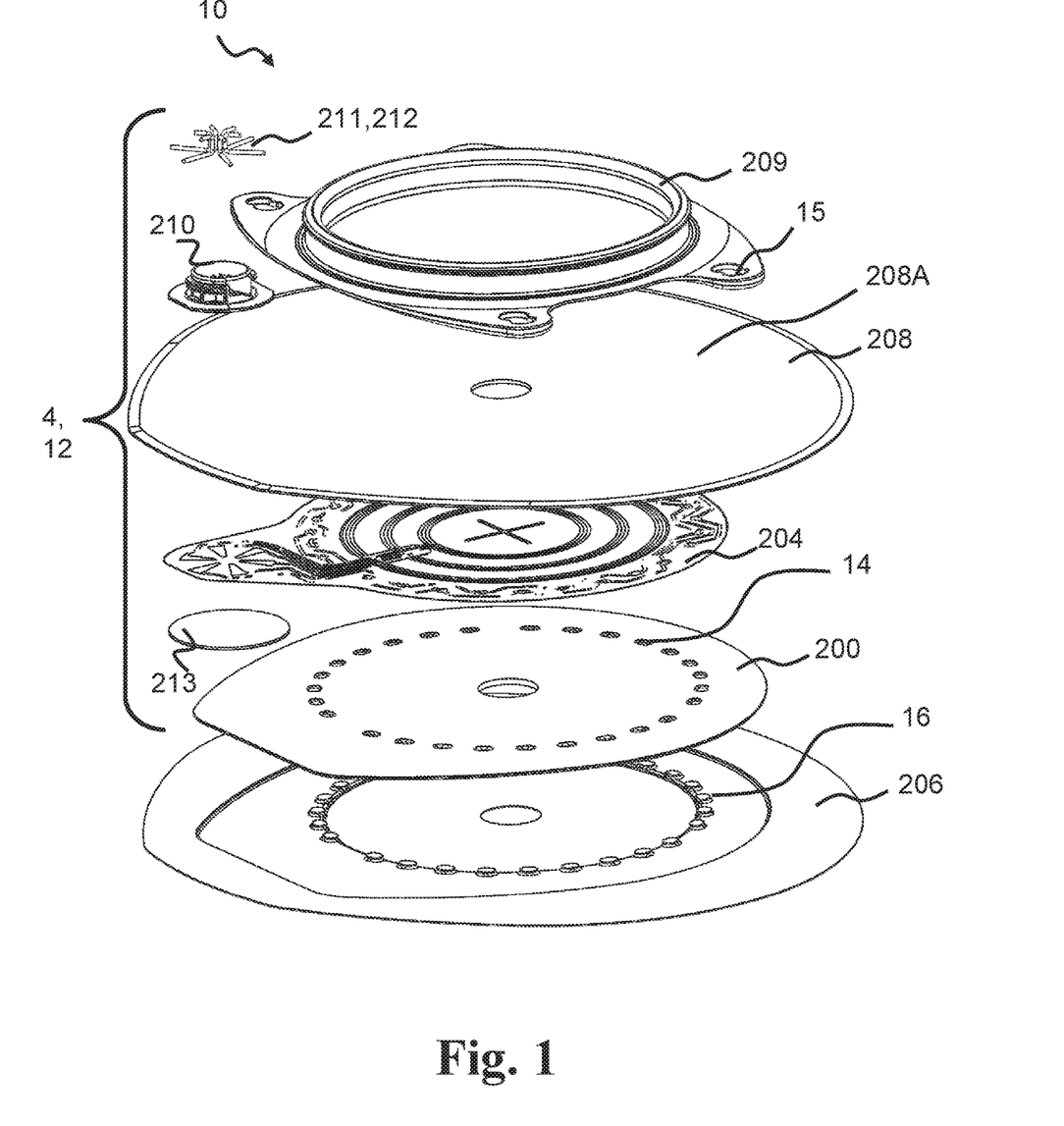
FIG. 1 is an exploded, perspective view of one embodiment of a system for preserving functionality of a skin-engageable element of an ostomy appliance during storage.

FIG. 1 is an exploded, perspective view of one embodiment of a system 10 for preserving functionality of a skin-engageable element 12 of an ostomy appliance during storage according to the disclosure.

FIG. 1 illustrates components of the system 10 including a skin-engageable element 12 of an ostomy appliance and a protective element 206. The skin-engageable element 12 forms a base plate 4 of the ostomy appliance. The skin-engageable element 12 includes a first layer of adhesive material 200 which includes two or more discrete through-going passages 14. In the embodiment of FIG. 1, a plurality of through-going passages 14 are provided in a circle (or circular) pattern. The skin-engageable element 12 further includes an electrode layer (or electrode assembly) 204 and a carrier sheet (or top layer) 208. In the embodiment of FIG. 1, the skin-engageable element 12 also includes a coupling ring 209 providing a first coupling half configured for coupling with a second coupling half on a body waste collecting bag (not shown). In embodiments, the coupling ring 209 forms part of an element also including one or more means 15 for attachment of an ostomy belt (not shown) or other means for supporting the skin-engageable element 12 of the ostomy appliance when attached to a user's peristomal skin surface. In embodiments, a body waste collecting bag (not shown) forms an additional component of the system 10. In other embodiments, a body waste collecting bag is permanently attached to the surface 208A of the second major distal side formed by the carrier sheet (top layer) 208.

In some implementations, as illustrated by FIG. 1, the base plate 4 can include a monitor interface. The monitor interface of the base plate includes a coupling part 210 for forming a mechanical connection, such as a releasable coupling between the monitor device and the base plate. The monitor interface of the base plate 4 can include a plurality of terminal elements respectively forming a plurality of terminals 212 for forming electrical connections with respective terminals of the monitor device. The coupling part 210 and the terminals 212 form a first connector 211 of the base plate 4. The base plate 4 includes a first intermediate element 213 on a distal side of the electrode assembly or electrode layer 204. The first intermediate element 213 is arranged between the terminal elements forming terminals 212 and the first adhesive layer 200.

FIG. 1 further illustrates embodiments wherein the protective element (release liner) 206 includes a sheet material including two or more discrete portions 16 projecting substantially axially from a major surface of the sheet material. The two or more discrete projecting portions 16 are adapted to engage with and enter into the two or more through-going passages 14 in the first layer of adhesive material 200. Because the projecting portions 16 are positioned in the through-going passages 14 during storage and until use, it is ensured that the adhesive material of the first layer of adhesive material 200 cannot "flow" or "seep" to make the through-going passage 14 collapse and become impassable during the storage. Thus, one effect of the projections 16 of the protective element 206 is that the through-going passages 14 do not clot and become useless before the user needs the product.

Other effects include protection of materials or components of the skin-engageable element of the ostomy appliance provided "underneath" one or more of the through-going passages in the adhesive material, such as materials or components configured to provide a signal when in contact with moisture passing through one or more of the through-going passages in the layer of adhesive material.

Whereas FIG. 1 illustrates a base plate 4 forming the skin-engageable element 12 of the ostomy appliance, one will realise that such base plate may be substituted with a sensor assembly part, e.g. comprising the first layer of adhesive material 200, the electrode layer 204, the first intermediate element 213, and optionally an encapsulating layer, e.g. a second layer of adhesive material. Thereby, said sensor assembly part may be configured for attachment to any generic base plate, such as the base plate comprising the carrier sheet 208 and the coupling ring 209 for attachment to a collecting bag.

Figure 2:
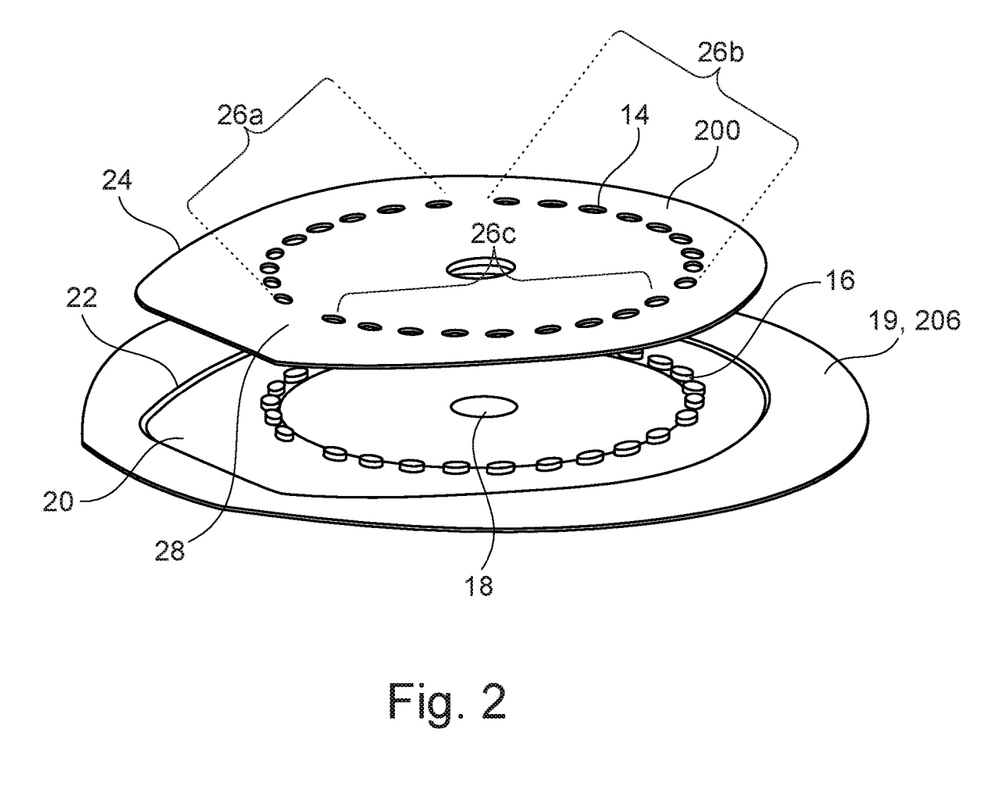
FIG. 2 is a schematic perspective view of one embodiment of a first layer of adhesive material and a protective element of the disclosed system.

FIG. 2 is a schematic perspective view of one embodiment of the first layer of adhesive material 200 and the protective element 206 of the system of the disclosure. The first layer of adhesive material 200 includes a plurality of through-going passages 14. The protective element 206 correspondingly includes a plurality of discrete projecting portions 16. Each of the projecting portions 16 is adapted to engage with a through-going passage 14. The protective element 206 is formed from a sheet material 19. Both the first layer of adhesive material 200 and the sheet material 19 of the protective element 206 are shown to include a stomal opening 18 in respective center portions thereof. In the embodiment illustrated in FIG. 2, the sheet material 19 of the protective element 206 includes a surface recess 20 having a contoured edge 22 corresponding to an outer edge contour 24 of the first layer of adhesive material 200. In some implementations, the corresponding edge contours 22, 24 can help to provide production advantages during manufacture.

It is further apparent from FIG. 2, that the protective element 206 may be provided for forming the first layer of adhesive material 200. For example, the first layer of adhesive material may be formed by scraping a layer of adhesive material onto the distal surface of the protective element 206, whereby the presence of the projecting portions 16 of the protective element 206 will result in the through going passages 14 being formed. Similarly, the contoured edge 22 may help form the outer periphery of the first layer of adhesive material 200.

FIG. 2 further illustrates embodiments wherein the through-going passages 14 of the first layer of adhesive material 200 and the corresponding projecting portions 16 of the protective element 206 being distributed in three or more distinct zones 26a, 26b, 26c. This manner of distributing the through-going passages 14 and the projecting portions 16 can help to define separate segments and/or locations on the base plate of the ostomy appliance. The distinct zones 26a, 26b, 26c are shown to be separated or divided by making a distance of a surface portion 28 between two "bordering" through-going passages 14 greater than a distance between two "neighbouring" through-going passages within a distinct zone 26a, 26b, 26c. Correspondingly, a distance is provided between "bordering" projecting portions 16 of the protective element 206.

Figure 3A:
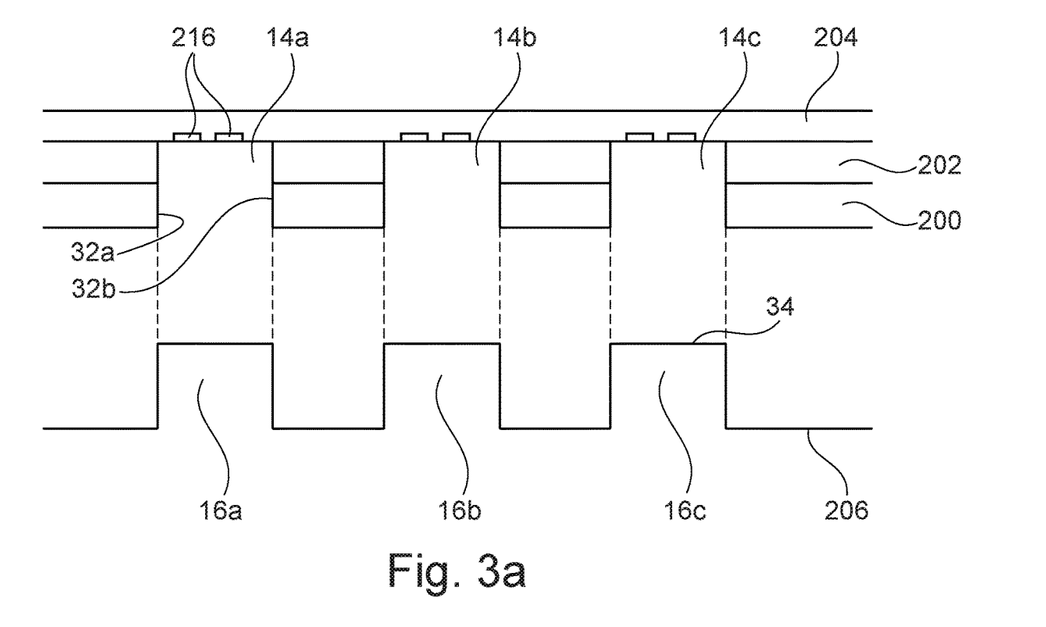
FIG. 3A is an enlarged, schematic cross-sectional sketch of one embodiment of a protective element of the system.

FIG. 3a is an enlarged, schematic cross-sectional sketch of the projecting portions 16 of the protective element 206 configured to engage with through-going passages 14 in the adhesive material. In the FIG. 3a sketch, three projecting portions 16 and corresponding through-going passages 14 are shown by way of example. Each discrete projecting portion 16 a, 16 b, 16 c engage with a corresponding individual (discrete) through-going passage 14 a, 14 b, 14 c. The embodiment of the skin-engageable element shown in FIG. 3a includes a first layer of adhesive material 200 and a second layer of adhesive material 202. The through-going passages 14 are shown to penetrate each of the first 200 and second layer of adhesive material 202. Thus, the through-going passages 14 may be considered coincident, which is to be interpreted such that a through-going passage in the first layer of adhesive material is right "on top" or "beneath" a through-going passage in the second layer of adhesive material without any substantial lateral offset between the passages of the two layers of adhesive material. The skin-engageable element also includes an electrode layer 204, in this case shown to include two individual electrodes 216 at each through-going passage 14 a, 14 b, 14 c. The projecting portions 16 a, 16 b, 16 c are illustrated above each through-going passage 14 a, 14 b, 14 c, however, punctured lines are intended to illustrate how the projections portions 16 a, 16 b, 16 c guide into and combine with the through-going passages 14 a, 14 b, 14 c, thereby protecting the electrodes 216 and stabilizing the internal "wall surface" 32 a, 32 b of each through-going passage 14 a, 14 b, 14 c. In embodiments, a distal-most surface portion 34 of each projecting portion 16 a, 16 b, 16 c is configured to be in direct contact with the electrode layer 204, alternatively directly contacting one or more of the electrodes 216.

Figure 3B:
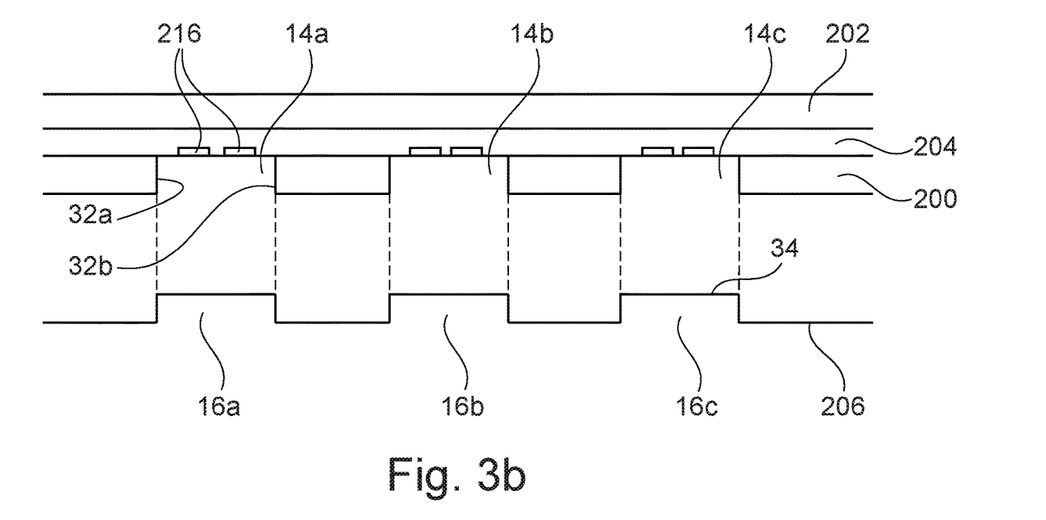
FIG. 3B is an enlarged, schematic cross-sectional sketch of a second embodiment of a protective element of the system.

FIG. 3b illustrates an enlarged, schematic cross-sectional sketch of the projecting portions 16 of the protective element 206 configured to engage with through-going passages 14 of the first layer of adhesive material 200. As illustrated, in such situation, the electrode layer 204 may be sandwiched between the first layer of adhesive material 200 and the second layer of adhesive material 202. However alternatively, the second layer of adhesive material 202 may be omitted. The extension of the projecting portions 16 is adapted to fit within the formed through-going passages 14 defined in the first layer of adhesive material 200. For example, such adapted fit involves adapting the extension of the projecting portions 16 to match the extension of the through-going passages 14.

Figure 4A:
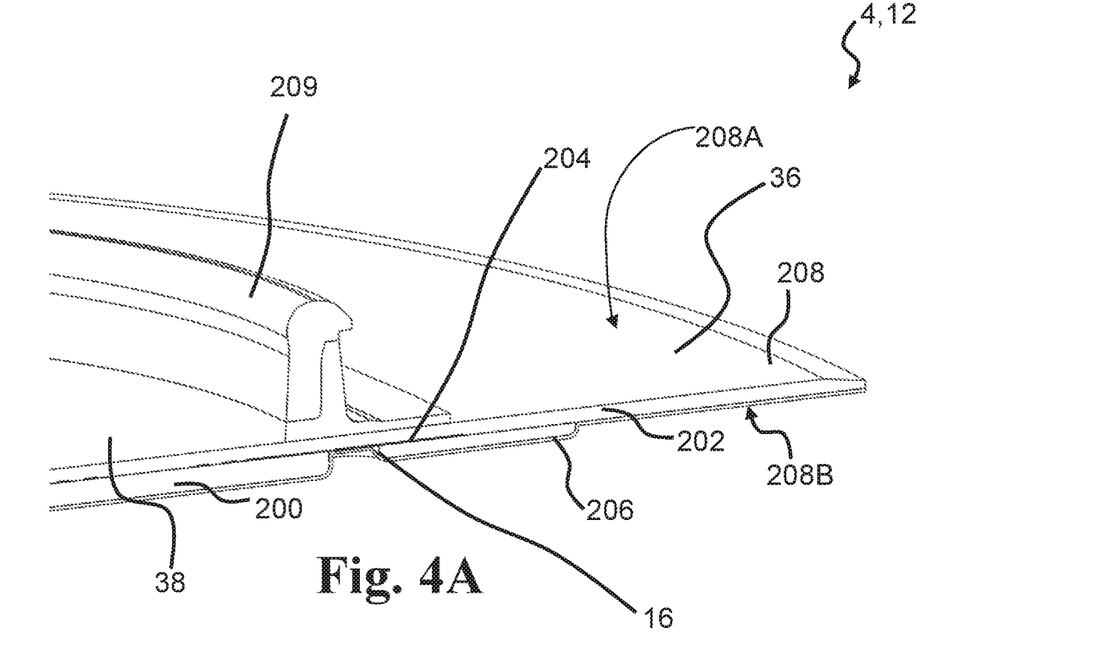
FIG. 4A is a perspective, cross-sectional view of a portion of one embodiment of the system.
Figure 4B:
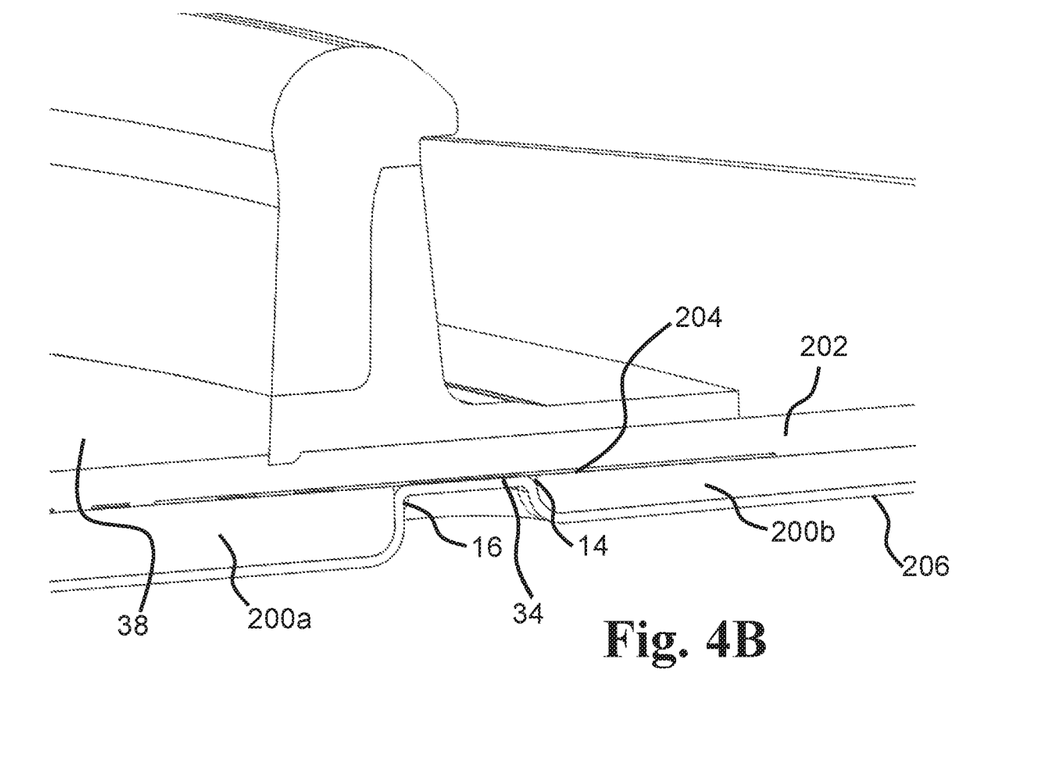
FIG. 4B is a perspective, cross-sectional view of a portion of the embodiment of the system of FIG. 4A.

FIGS. 4A and 4B are perspective, cross-sectional views of a portion of one embodiment of a system according to the disclosure, with FIG. 4B being an enlarged view of a portion of FIG. 4A and showing less of a rim portion 36 of a skin-engageable element 4, 12 of the system. The views illustrate the skin-engageable element 4, 12 including carrier sheet 208, which can be seen to form a majority of the second major distal side of the skin-engageable element 12 and defining surface 208A. The skin-engageable element 4, 12 includes a first layer of adhesive material 200 and a second layer of adhesive material 202 forming a first major proximal side of the skin-engageable element 12, and defining surface 208B. The second layer of adhesive material 202 forms a rim adhesive of the skin-engageable element 4, 12. A radial extent of the first layer of adhesive material 200 is less than a radial extent of the second layer of adhesive material 202. In the embodiment of FIGS. 4A, 4B, a center portion 38 of the first layer of adhesive material 200 forms a center adhesive of the skin-engageable element 12, which is of greater thickness than a thickness of the second layer of adhesive material 202. The center adhesive is shown to be of greater thickness than the rim adhesive. The skin-engageable element 4, 12 further includes an electrode layer 204 provided generally between the first layer of adhesive material 200 and the second layer of adhesive material 202.

FIGS. 4A and 4B further illustrate embodiments wherein a coupling ring 209 is attached to the second major distal side formed by the carrier sheet 208 (surface 208A). A protective element or release liner 206 is removably attached to the first major proximal side of the skin-engageable element 12 including the first and second layers of adhesive materials 200, 202. The protective element or release liner 206 is illustrated with one of two or more discrete projecting portions 16 engaging with one of two or more through-going passages 14 in the first layer of adhesive material. In the illustrated embodiment, the second layer of adhesive material 202 is provided distal to the electrode layer 204 and does not include any through-going passages coinciding with the through-going passages of the first layer of adhesive material 200. Instead, a distal-most surface portion 34 of the projecting portion 16 directly engages (abuts) the electrode layer 204 or the actual electrode(s). Further, in the illustrated embodiment, a thickness of a portion of the first layer of adhesive material 200 provided radially outside of the projecting portion 16/the through-going passage 14, is less than a thickness of a portion of the first layer of adhesive material 200 provided radially inside of the projecting portion 16/the through-going passage 14.

FIG. 4B also illustrates an embodiment, wherein a thickness (measured in the axial direction of the skin-engageable element 4, 12) of a portion 200b of the first layer of adhesive material 200 provided radially outside of the through-going passage 14, is smaller than a thickness of a portion 200a provided radially inside of the through-going passage 14. In the embodiments of FIG. 4B, the provision of the projecting portions 16 of the protective element 206 are particularly advantageous in that the portions 16 protect the otherwise exposed (not first adhesive covering) electrode layer 204 from the proximal side, while the electrode layer 204 in these embodiments is protected on the distal side by the second layer of adhesive material 202. This helps to also preserve the functionality of the one or more electrodes of the electrode layer 204 of the system during storage.

Figure 5:
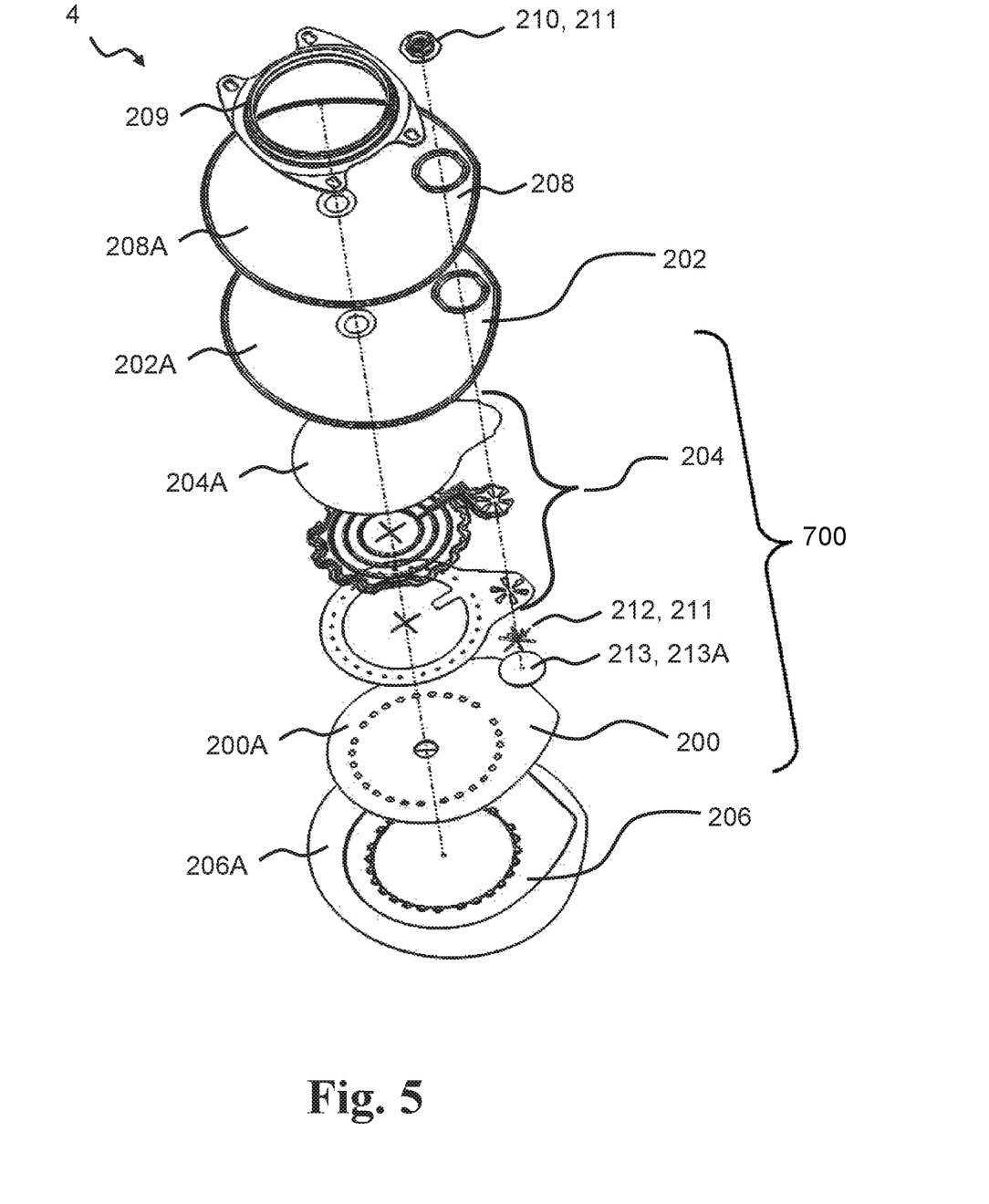
FIG. 5 is an exploded, perspective view of one embodiment of a base plate of an ostomy appliance formed by a skin-engageable element of the system.

FIG. 5 illustrates an exploded view of one exemplary embodiment of a skin-engageable element provided as a base plate of an ostomy appliance. The base plate 4 comprises a first adhesive layer 200. A proximal surface of the first adhesive layer 200 is configured to adhere to the user's skin in the peristomal area and/or potentially to additional seals, such as sealing paste, sealing tape and/or sealing ring. The base plate 4 in embodiments optionally comprises a second adhesive layer 202, also denoted rim adhesive layer. The illustrated embodiments of the base plate 4 comprises a plurality of electrodes arranged in an electrode assembly 204, e.g. forming an electrode layer. The electrode assembly or electrode layer 204 is arranged between the first adhesive layer 200 and the second adhesive layer 202.

As previously described, some parts of the illustrated base plate 4 may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate. In the embodiment of FIG. 5, the electrode assembly or electrode layer 204 comprises a support layer with electrodes formed on a proximal surface of the support layer. The skin-engageable element or base plate 4 and/or the sensor assembly part 700 comprises a protective element in the form of a release liner 206 which is configured to be removed by the user prior to applying the base plate 4 on the skin. The base plate 4 of the illustrated embodiment further comprises a top layer or carrier sheet 208 and a first coupling half in the form of a coupling ring 209 for coupling an ostomy pouch to the base plate 4. In the embodiment of FIG. 4, the top layer or carrier sheet 208 also functions as a protective layer protecting the second adhesive layer 202 from external strains and stress during use of the skin-engageable element or base plate 4.

Figure 6:
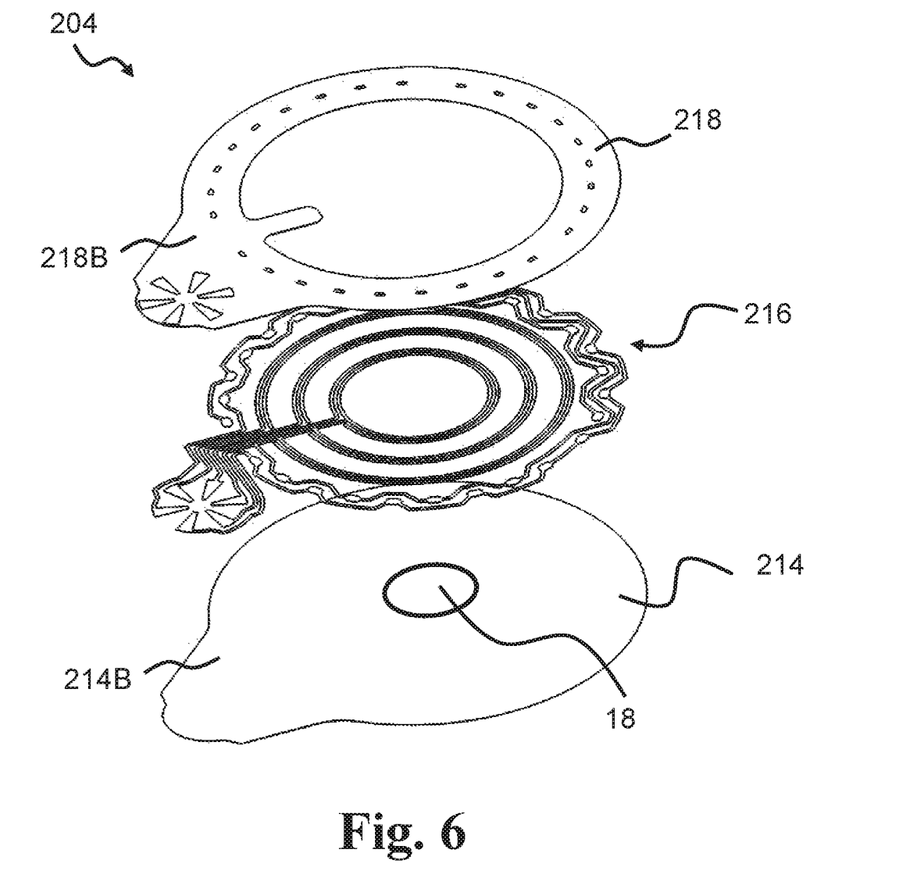
FIG. 6 is an exploded, perspective view of one embodiment of an electrode layer of a skin-engageable element for an ostomy appliance of the system.

FIG. 6 is an exploded view illustrating one embodiment of an exemplary electrode assembly or electrode layer 204 of a skin-engageable element of a system as disclosed herein. In the illustrated embodiment, the electrode assembly or electrode layer 204 comprises a support layer 214 with a proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of a monitor interface. Further, the illustrated electrode assembly or electrode layer 204 comprises a masking element 218 with proximal surface 218B configured to insulate electrode parts of electrodes 216 from the first adhesive layer of the base plate. The masking element 218 covers or overlaps with parts of the electrodes 216 when seen in an axial direction. Also illustrated is a center opening 18 in the support layer 214 and adapted to receive a user's stoma.

Figure 7:
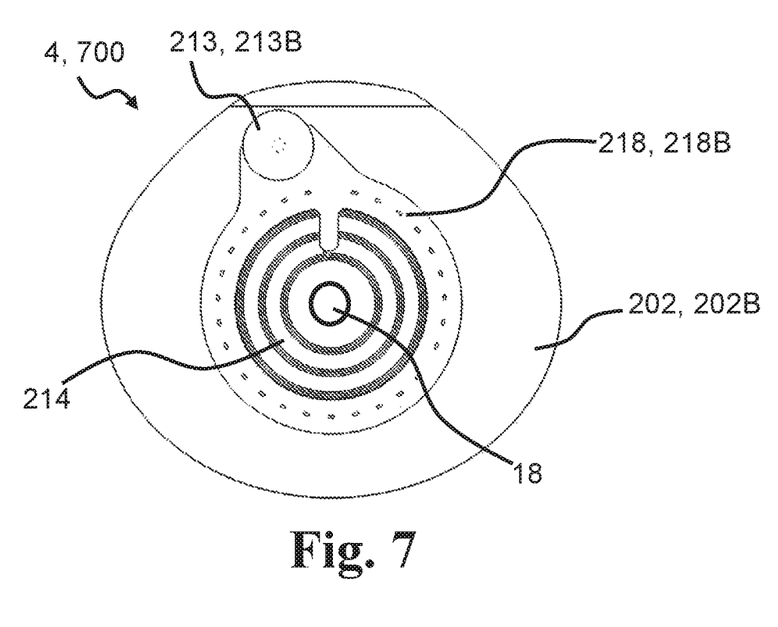
FIG. 7 is a proximal view of proximal surfaces of one embodiment of parts of a skin-engageable element of the system, with the first adhesive layer and the protective element of the system removed for illustration purposes.

FIG. 7 is a proximal view of proximal surfaces of one embodiment of parts of a skin-engageable element provided as a base plate without showing a first adhesive layer 200 and a protective element in the form of a release liner 206. The base plate 4 and/or the sensor assembly part 700 comprises a first intermediate element 213 on the proximal side of the electrode assembly or electrode layer 204, i.e. between the electrode assembly or electrode layer and the first adhesive layer (not shown). The first intermediate element 213 covers the terminal elements of the base plate 4 and/or the sensor assembly part when seen in the axial direction, and protects the first adhesive layer from mechanical stress from the terminal elements of the base plate and/or the sensor assembly part.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

LIST OF REFERENCE NUMBERS IN DRAWINGS 4 base plate
10 system
12 skin-engageable element
14a-c through-going passage in adhesive material
15 attachment means for ostomy belt
16 projecting portion of protective element/release liner
18 stomal opening
19 sheet material
20 surface recess
22 contoured edge of surface recess
24 outer edge contour of first layer of adhesive material
26a-c distinct distribution zones
28 surface portion
32a-b internal "wall surface" of through-going passage
34 proximal-most surface portion of projecting portion
36 rim portion
38 center portion
200 first layer of adhesive material/first adhesive layer
202 second layer of adhesive material/second adhesive layer
204 electrode layer/electrode assembly
206 protective element/release liner
206A distal surface of the release liner
206B proximal surface of the release liner
208 carrier sheet
208A distal surface of the carrier sheet
208B proximal surface of the carrier sheet
209 coupling ring
210 coupling part of first connector
211 first connector
212 terminals of first connector
213 first intermediate element
214 support layer of electrode layer/electrode assembly
214A distal surface of support layer
214B proximal surface of support layer
216 electrodes of electrode layer/electrode assembly
218 masking element
218A distal surface of masking element
218B proximal surface of masking element

The invention claimed is:

1. A system for preserving functionality of a skin-engageable element of an ostomy appliance during storage, comprising:
a skin-engageable element comprising a carrier sheet and having a first major proximal side and a second major distal side, the skin engageable element comprising, on the first major proximal side, a first layer of adhesive material, which is configured for adhesion of the skin-engageable element to a peristomal skin portion of a user, wherein the first layer of adhesive material comprises a proximal surface and a distal surface and two or more discrete through-going passages extending entirely through the first layer of adhesive material from the proximal surface to the distal surface; and
a protective element removably attached to the first major proximal side of the skin-engageable element, the protective element comprising a sheet material comprising two or more discrete portions projecting substantially axially from a major surface of the sheet material,
wherein each of the two or more discrete projecting portions of the sheet material is adapted to engage with a through-going passage in the first layer of adhesive material, and
wherein each through-going passage in the first layer of adhesive material is open and passable, when the protective element is removed from the skin-engageable element.

2. The system of claim 1, wherein the skin-engageable element comprises a second layer of adhesive material distal to the first layer of adhesive material.

3. The system of claim 2, wherein a total second surface area of the second layer of adhesive material is greater than a total first surface area of the first layer of adhesive material.

4. The system of claim 1, wherein the skin-engageable element further comprises one or more electrodes provided distal to the first layer of adhesive material, wherein the one or more electrodes is/are accessible from the first major proximal side, through the two or more discrete through-going passages in the first layer of adhesive material.

5. The system of claim 4, wherein the skin-engageable element comprises a second layer of adhesive material distal to the first layer of adhesive material, and wherein the one or more electrodes are provided proximal to the second layer of adhesive material.

6. The system of claim 4, wherein the one or more electrodes is/are provided in an electrode layer, wherein the electrode layer comprises material of the electrode(s) provided in a layer of polyurethane material.

7. The system of claim 6, wherein the skin-engageable element comprises a second layer of adhesive material proximal to the first layer of adhesive material, and wherein a total third surface area of the electrode layer corresponds substantially to a total second surface area of the second layer of adhesive material.

8. The system of claim 6, wherein a total third surface area of the electrode layer corresponds substantially to a total first surface area of the first layer of adhesive material.

9. The system of claim 1, wherein the second major distal side of the skin-engageable element further comprises a first coupling half provided on the carrier sheet and adapted to be coupled to a second coupling half on a collecting bag for collecting body waste.

10. The system of claim 9, wherein the first coupling half comprises an annular ring extending substantially perpendicularly from a flange, and wherein an outermost periphery of the flange is substantially at a same radial distance from a center of the skin-engageable element as an outermost periphery of the electrode layer.

11. The system of claim 1, wherein the two or more discrete projecting portions projecting from the protective element comprise a plurality of discrete projecting portions.

12. The system of claim 11, wherein the plurality of discrete projecting portions projecting from the protective element is distributed in a circle pattern.

13. The system of claim 11, wherein the plurality of discrete portions projecting from the protective element comprises 2-50 discrete projecting portions.

14. The system of claim 13, wherein the plurality of discrete portions projecting from the protective element comprises 21-30 discrete projecting portions.

15. The system of claim 1, wherein the skin-engageable element comprises a central opening for receiving body waste and/or for accommodating a stoma.

16. The system of claim 1, further comprising a collecting bag for collecting of body waste, the collecting bag configured to be attached or coupled to the second major distal side.

17. A protective element attachable to a proximal adhesive layer of a layered structure having an electrode layer sandwiched between the proximal adhesive layer and a distal adhesive layer, wherein the protective element is configured to be releasable from the proximal adhesive layer of the layered structure, wherein the protective element comprises a sheet material, the sheet material comprising two or more discrete portions projecting substantially axially from a major surface of the sheet material, wherein the proximal adhesive layer comprises a proximal surface and a distal surface and comprises at least two through-going passages extending from the proximal surface through the distal surface to the electrode layer, and wherein the two or more discrete portions of the sheet material engage with the at least two through-going passages of the adhesive layer.

18. The system of claim 1, wherein each of the two or more discrete portions of the sheet material extend within an entirety of each of the at least two discrete through-going passages of the adhesive layer.

19. The system of claim 6, wherein the two or more discrete portions of the sheet material have a distalmost surface that directly contacts the electrode layer and the one or more electrodes.

20. A system for preserving functionality of a skin-engageable element of an ostomy appliance during storage, comprising:
    a skin-engageable element comprising a carrier sheet and having a first major proximal side and a second major distal side, the skin engageable element comprising, on the first major proximal side, a first layer of adhesive material, which is configured for adhesion of the skin-engageable element to a peristomal skin portion of a user, wherein the first layer of adhesive material comprises a proximal surface and a distal surface and two or more discrete through-going passages extending from the proximal surface to the distal surface; and
    a protective element removably attached to the first major proximal side of the skin-engageable element, the protective element comprising a sheet material comprising two or more discrete portions projecting substantially axially from a major surface of the sheet material,
    wherein each of the two or more discrete projecting portions of the sheet material is adapted to engage with an entirety of each of the two or more discrete through-going passage in the first layer of adhesive material, and
    wherein each through-going passage in the first layer of adhesive material is open and passable, when the protective element is removed from the skin-engageable element.

* * * * *